United States Patent [19]

Favonio

[11] Patent Number: 5,046,950
[45] Date of Patent: Sep. 10, 1991

[54] APPARATUS AND METHOD FOR CARRYING OUT DEVITALIZATIONS AND ROOT CANAL TREATMENTS IN TEETH, AND FOR SEALING THE TREATED TEETH

[75] Inventor: Osvaldo Favonio, Ornago, Italy

[73] Assignee: FARO Fabbrica Apparecchiature Razionali Odontoiatriche S.p.A., Milan, Italy

[21] Appl. No.: 592,741

[22] Filed: Oct. 4, 1990

[30] Foreign Application Priority Data

Oct. 4, 1989 [IT] Italy ............................... 21915 A/89
Dec. 20, 1989 [IT] Italy ............................... 22764 A/89

[51] Int. Cl.$^5$ ............................................. A61G 5/02
[52] U.S. Cl. ....................................... 433/81; 433/224
[58] Field of Search ...................... 433/81, 91, 92, 95, 433/224, 226

[56] References Cited

U.S. PATENT DOCUMENTS 3,079,690  5/1963  Lödige ................................. 433/81
3,704,520  12/1972 Weissman .
4,021,921  5/1977  Detaille .

FOREIGN PATENT DOCUMENTS 0201119 12/1986 European Pat. Off. ............... 433/91
0299919  1/1989 European Pat. Off. ............. 433/224
2342824  3/1974 Fed. Rep. of Germany ...... 433/224
1412766  7/1988 U.S.S.R. ............................... 433/81

Primary Examiner—Cary E. O'Connor
Attorney, Agent, or Firm—Diller, Ramik & Wight

[57] ABSTRACT

An improved apparatus for carrying out devitalizations and root canal treatments in teeth by means of the use of liquid chemical substances comprises the following steps: putting the pulp chamber and the relevant root canals under vacuum by means of a vacuum vessel; and selectively feeding, in succession, into the pulp chamber and the root canals liquid chemical substances, which are contained inside respective containers under atmospheric pressure; the substances are then drawn into said vacuum vessel. The so treated tooth is then sealed by sucking a sealing paste-like substance into it.

14 Claims, 1 Drawing Sheet

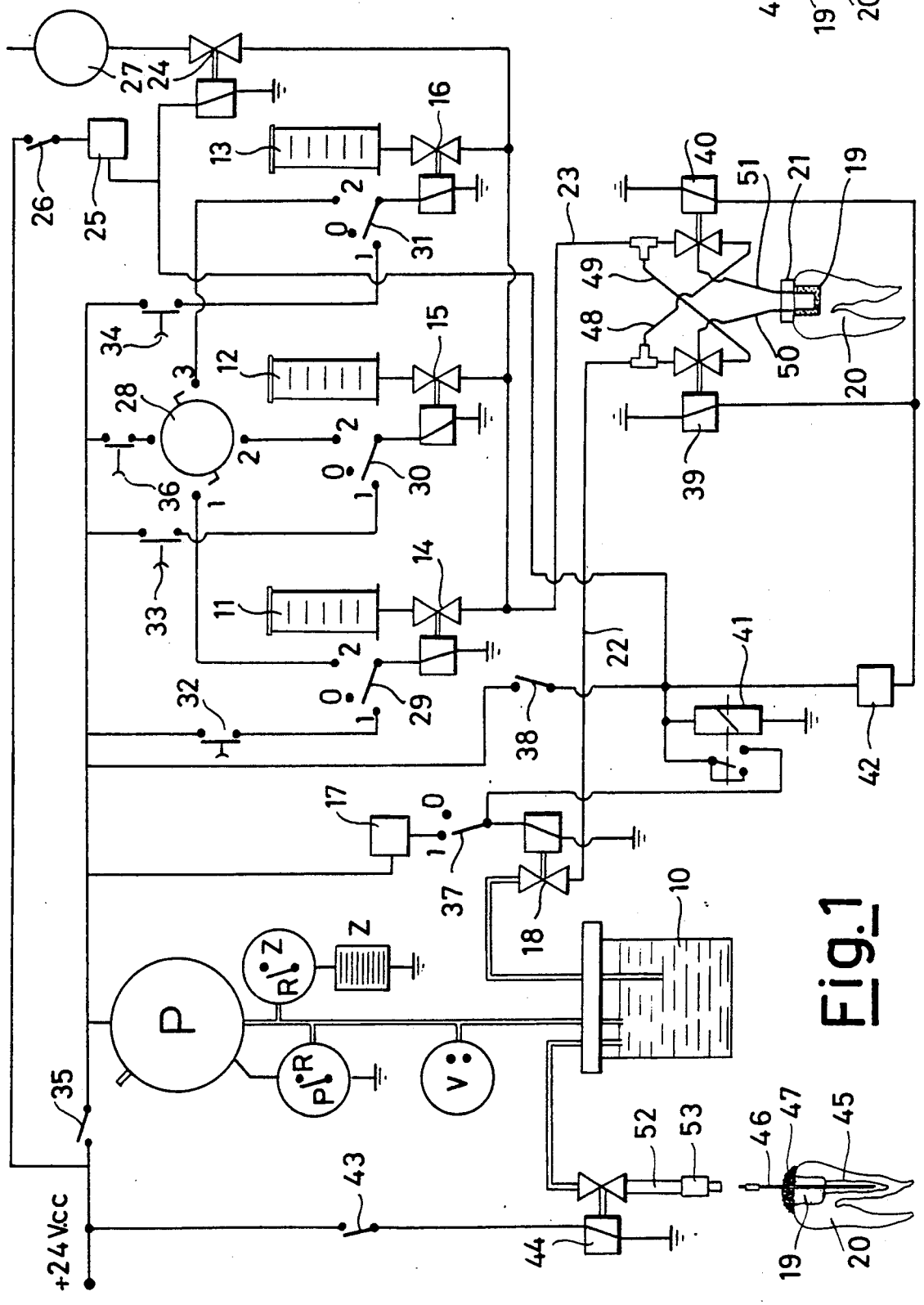

5,046,950

APPARATUS AND METHOD FOR CARRYING OUT DEVITALIZATIONS AND ROOT CANAL TREATMENTS IN TEETH, AND FOR SEALING THE TREATED TEETH

The present invention relates to an improved apparatus for carrying out devitalizations and root canal treatments in teeth by means of the use of liquid chemical substances.

The present invention relates furthermore to a particularly advantageous method for sealing, by means of a paste-like substance, the pulp chamber and the root canals of a tooth submitted to devitalization and root canal treatment.

In dental medicine, the use of special instruments for effecting canal treatments has been long known.

However, the mechanical intervention with suitable instruments involves a plurality of serious problems.

In fact, the use of these instruments implies a mechanical action on the concerned part, which involves the opening and reaming of the root canal in order to be able to devitalize the tooth by means of the removal—still by means of mechanical instruments—of the nerve.

Such an operating system generally requires a certain number of sittings which should only be carried out by very qualified and skilled people, above all if one wants to obtain a perfect devitalization, as well as the elimination of any possibly existing abscesses or granulomas, and the like.

Finally the necessary time, required for successfully performing such an operation, when traditional mechanical instruments are used, is considerably long.

In an attempt to obviate the above cited drawbacks, other intervention systems were suggested, according to which the pulp chamber and the root canals are washed and emptied by delivering pressurized chemical liquids into them.

Such a system is disclosed, e.g., in Italian patent N. 1185556, and in U.S. Pat. No. 4,021,921. However, the use of pressurized chemical liquid showed to be not completely effective in that, during the treatments, occlusions of the root canals occur, which are caused by the pulp contained under pressure inside the tooth chamber, with the consequent impossibility of access of the liquid used for the treatment.

U.S. Pat. No. 3,704,520 also proposed to open a canal in the tooth, to extract the pulp by suction and to wash the root canal by means of a washing liquid, in order to extract the residual pulp.

Such a system showed to be inadequate owing to the difficulties which were met in sucking the totality of the pulp directly from the opened canal, and due to the fact that the subsequent feed of the washing liquid causes, also in this case, an occlusion of the root canals by the same pulp submitted to the pressure of the washing liquid delivered.

In addition, as those skilled in the art are well aware of, in a tooth submitted to devitalization and canal treatment, at the end of the treatment, the pulp chamber and the root canals must be perfectly tightly closed by means of the use of a sealing material, in order to prevent variour kinds of infections from possibly arising at a later time.

Unfortunately, the several techniques proposed heretofore in order to close the canals do not secure a total filling of the root canals, in particular when the latter are more than one, of small size, and bent.

A purpose of the instant invention is of obviating the drawbacks of the prior art by providing an apparatus which, by using liquid chemical treatment substances, is capable of removing the interdental pulp, the nerve and any possible infected parts from the treated region in one short sitting and, of course, without the use of mechanical instruments and highly specialized personnel being required.

In view of such a purpose, according to the present invention, the instant Applicant thought of providing an apparatus for carrying out devitalizations and canal treatments in teeth, of the type in which liquid chemical treatment substances are fed into the pulp chamber and root canals of the tooth, characterized in that it comprises, in combination: sealing means for tightly sealing said pulp chamber, a tightly sealed vessel, means for putting said vessel under controlled vacuum, first selective connection means between said vessel and said pulp chamber, a plurality of atmospheric pressure containers suitable for containing respective liquids for the treatment of the pulp chamber and of the root canals, second selective connection means between said plurality of containers and said pulp chamber, and third selective connection means between said pulp chamber and atmosphere, so that the pulp chamber and the root canals can be firstly put under vacuum and then treated in succession with said treatment liquids at atmospheric pressure, which liquids are drawn into said vessel under controlled vacuum, flowing through said pulp chamber and the relevant root canals.

Preferably, the level of vacuum inside the pulp chamber is submitted to changes a plurality of times, at short time intervals over a predetermined time period.

For example, said vacuum level can be submitted to said changes with a frequency of 40 times per minute.

In an analogous way, the pulp chamber can be selectively connected with each of the containers containing the respective treatment liquids a plurality of times, at short time intervals over a predetermined time period.

For example, the frequency of these changes of connections is of 20 times per minute.

The apparatus operates under reduced pressure: for example, the values of vacuum can be comprised within the range of from 0.526 to 0.592 atm.

Another purpose of the present invention is of providing a sealing apparatus and equipment for sealing the treated tooth, such that the paste-like treatment substance can be applied to the tooth in such a way that such paste-like treatment substance completely fills the tooth, sealing with perfect tightness both the root canals and the overhanging pulp chamber.

In view of such a purpose, according to the instant invention the present Applicant thought of providing a method for tightly sealing, by means of a paste-like substance, the pulp chamber and the root canals of a tooth previously submitted to devitalization and canal treatment, which method comprises the steps of:

prearranging, inside the tooth, connection means suitable for connecting said root canals with a vacuum source;

filling the pulp chamber of the tooth with said paste-like substance, such as to tightly seal the underlying root canals;

connecting said connection means with the vacuum source;

applying vacuum to the interior of the root canals, such as to cause a portion of said paste-like substance, contained inside the pulp chamber, to be sucked into said root canals;

finally, removing said connection means from the tooth.

According to a preferred form of practical embodiment of the invention, said connection means suitable for connecting the root canals with a vacuum source are constituted by hollow needles which are freely introduced into the root canals before the paste-like filling substance is fed into the pulp chamber.

Said vacuum source is preferably constituted by a vessel which is evacuated by means of a vacuum pump, and is connected with the hollow needles by means of a pipe ending with a fitting for tightly connecting said pipe with the same needles, and with the interposition of a valve which controls the application of vacuum.

The structural and functional characteristics of the invention and its advantages over the technique known from the prior art will be still more evident from an examination of the following disclosure made by referring to the hereto attached drawings, which schematically show an example of apparatus according to the same invention.

In the drawings:

FIG. 1 schematically shows an example of an apparatus accomplished according to the present invention; and FIG. 2 shows the end step, of tight sealing of the treated tooth.

Referring to FIG. 1, the apparatus according to the present invention is structurally constituted by a vacuum pump P operating, e.g., at pressure values comprised within the range of from 0.526 to 0.592 atm, a pressure regulator PR, a vacuum indicator V, a special limiting pressure regulator RZ comprising a device Z for warning that the limit safety vacuum has been reached. This section of the apparatus according to the present invention is completed by a tightly sealed vessel 10 which, as is better explained in the following, acts both as a vacuum tank and as a collecting tank for the sick tissues removed.

The apparatus comprises furthermore three containers 11, 12 and 13, each equipped with a respective electrovalve 14, 15 and 16 for selectively connecting said containers with the pulp chamber 19 of a tooth 20.

An oscillator 17 with a control switch 37 controls an electrovalve 18 for selectively connecting said vessel 10 with the pulp chamber 19 of said tooth 20.

A plug 21 is suitable for tightly sealing the pulp chamber 19 of the tooth 20 and into it extensions 50, 51 of ducts 22, 23 open which respectively connect the pulp chamber 19 with said vacuum vessel 10 and the containers 11, 12 and 13. Between said ducts 22, 23 and said extensions 50, 51 respective electrovalves 39, 40, which control the flow, and bypass ducts 48, 49 are installed. Said electrovalves 39, 40 are piloted by means of a frequency generator 42, which is turned on by means of a switch 38 from which the relay 41, the electrovalve 18 and the electrovalve 24 are excited simultaneously.

Said duct 23 can be furthermore connected with atmosphere—with the interposition of an air filter 27—through an electrovalve 24 which is controlled by the switch 38. A switch 26 is furthermore provided, which can control the same electrovalve 24 through an oscillator 25.

The selection of the treatment liquid contained inside the containers 11, 12 and 13 is carried out by means of a central change-over switch 28, through respective multi-way switches 29, 30 and 31. Pushbutton switches 32, 33 and 34 enable the operator to respectively command, at time intervals, the opening of the electrovalves 14, 15 and 16. The reference numeral 35 indicates the main switch 35 for turning on/off the apparatus, which operates at 24 V, and the reference numeral 36 indicates a pushbutton switch 36 which controls the electrovalves 14, 15 and 16.

The apparatus is completed by a pipe 52 ending with a fitting 53 for a hollow needle 46. Said pipe 52 is connected with the vacuum vessel 10 with the interposition of an electrovalve 44 which is controlled by means of a switch 43.

The operation of the apparatus according to the present invention is clear from what is disclosed above by referring to the drawing and, in brief, is as follows.

For exemplifying, non-limitative purposes, the operation is disclosed in the following of the apparatus used for the canal treatment of a tooth 20 with two roots.

After suitably opening the pulp chamber 19 by conventional means (turbine), the plug 21 is fixed by suitable mastic, so as to seal the tooth with perfect tightness.

Having done this, the main switch 35 is switched on. The pump P is started. The pump P is stopped by the regulator PR, e.g., when the vacuum indicator indicates that inside the tank 10 the operating vacuum e.g., a residual pressure of about 0.590 atm, is reached.

During this step, the electrovalve 18 is closed.

The switch 37 is now switched on (position 1) in order to start the oscillator 17 which causes the electrovalve 18 to open, thus putting the vacuum tank 10 into communication with the pulp chamber 19 through the duct 22.

Thanks to the oscillator 17, which continuously opens and closes at prefixed time intervals, the tank 10 and the pulp chamber 19 can be connected with each other at short time intervals, e.g., with a frequency of 40 times per minute, with dIfferent vacuum levels being thus achieved. This action, lasting for example 2 minutes, yields highly positive results from the view point of the further cleaning of the canals, which are submitted to different vacuum levels.

After this time period, the multi-way switch 29 is moved to position 2 and the multi-way switch 28 is moved to position 1.

The oscillator 17, normally closed, is opened by moving the switch 37 to position 0 (the switch 37 is switched off) with the pushbutton 36 being simultaneously pressed, so as to cause the electrovalve 14 to open with the liquid contained inside the container 11 being thus caused to flow into the pulp chamber 19.

By switching on the switch 37 (position 1), the oscillator 17 is then started again; the electrovalve 18 is caused to open and the pulp chamber 19 is connected with the vacuum tank 10.

While the tank 10 and the pulp chamber 19 are connected with each other, the oscillator 17 causes the electrovalve 18 to close and open in sequence at time intervals, so that inside the pulp chamber 19 changes will occur in vacuum values; the opening/closing frequency of the electrovalve 18 will be, e.g., of about 40 times per minute.

During the just disclosed step, the opening of the electrovalve 18 ensures that, should an operating abnormality occur (such as, e.g., a poor seal or even the escape of the plug 21 from the pulp chamber 19), the treatment liquid will be sucked into the vessel 10, therefore without any leakages thereof into the oral cavity of the patient.

The switch 26 is now switched on in order to start the oscillator 25 which causes the electrovalve 24 to open. The opening of the electrovalve 24 puts the duct 23, and therefore the pulp chamber 19, the duct 22 and the tank 10 into communication with atmosphere.

Then the multi-way switch 29 is moved back to position 1 and the pushbutton 32 is pressed at time intervals, so that the liquid contained inside the container 11 will be drawn through the electrovalve 14 into the pulp chamber and from there, through the open electrovalve 18, into the vessel 10.

For instance, the pushbutton 32 can be pressed at a rate of about 1 time per second, which action will cause, through a sequence of pressure and vacuum pulses—obtained thanks to the opening and closure of the electrovalve 24 controlled by the oscillator 25—the removal to take place from the pulp chamber of the those parts which are contained inside said chamber and have to be eliminated from it. Such removed parts are collected inside the vessel 10.

After the desired time of treatment by pressure and vacuum pulses, the oscillator 25 is deenergized by switching off the switch 26, with the electrovalve 24 being hence closed.

At this point, the apparatus is ready for the treatment with the next liquids contained inside the containers 12 and 13. This treatment is carried out by performing the same operations as disclosed above by referring to container 11, by simply switching the multi-way switch 28 to position 2 for container 12 and to position 3 for container 13, and acting on the respective pushbuttons 33 and 34.

These operations, in the aforesaid sequences, can be repeated, for example, five times with a chemical treatment liquid contained inside container 11 (by acting on pushbutton 32); three times with an enzymatic liquid contained inside container 12 (by acting on pushbutton 33) and twice with an end washing liquid contained inside container 13 (by acting on pushbutton 34).

If one wishes to reduce the treatment cycle times, the process can also be carried out as follows.

After that each treatment liquid (respectively contained in containers 11, 12 and 13) has been fed into the pulp chamber as disclosed hereinabove, the switch 38 is switched on.

When switch 38 is switched on, the relay 41 closes and in its turn opens the electrovalve 18 and the electrovalve 24, and finally excites the frequency generator 42.

The frequency generator 42 performs the task of exciting simultaneously the electrovalves 39 and 40, with a square-wave frequency of about 120 Hz, so as to obtain a fluid alternation determined as follows: during the first half second (60-120 Hz) there is a flow of liquid, under a pressure of 0.4 bar, through the pipe 23, through the electrovalve 40. Said liquid enters the pulp chamber of tooth 20 through the pipe 51 and then continues its flow through the pipe 50 and the electrovalve 39, through the pipe 22 and the electrovalve 18, and then ends its flow inside the vessel 10.

During the next half second (60-120 Hz), the liquid will flow along the following path: pipe 23, pipe 49, electrovalve 39, pipe 50, tooth 20, pipe 51, electrovalve 40, pipe 48, pipe 22, vessel 10.

Finally, the switch 38 is switched off, the switches 37 and 26 are switched on for some tens of seconds, and then are switched off again.

Thanks to the treatment liquid flowing in alternate directions, a perfect cleaning of the pulp chamber and of root canals can be obtained always, and within very short times.

At this point the cycle is ended. A number of such cycles will be performed, which will be as large as deemed suitable.

After devitalization and canal treatment being carried out as disclosed hereinabove, the tooth can be sealed by inserting the hollow needle 46 to the apex of the root canal 45. The opening provided in the pulp chamber 19 is closed with a right amount (with a slight excess) of sealing paste 47, being careful of eliminating any air leaks; the pipe 52 is then connected with the hollow needle 46. At this point, by switching on the switch 43 the electrovalve 44 which connects the vacuum tank 10 with the root canal 45 is opened. Thanks to the so generated vacuum, the sealing paste 47, previously deposited on the opening of the pulp chamber 19 is sucked into the root canal 45, filling it perfectly (FIG. 2). The switch 43 is opened, the electrovalve 44 gets closed, the hollow needle 46 is removed from the canal 45 and the sealing operation is concluded.

The pipe 52 may end with a plurality of fittings 53 for a plurality of hollow needles 46, for the simultaneous treatment of a plurality of canals of a same tooth.

The advantages of the apparatus constructed in accordance with the present invention can be summarized as follows.

The work carried out in the pulp chamber and in the root canals is mainly done under vacuum and under atmospheric pressure. The purpose of the vacuum created inside the sealed system constituted by the machine, the pulp chamber and the root canals is firstly of enabling the chemical liquids to perform their action, and thus shift and remove the interdental pulp and nerve, and secondly of obtaining the absolute safety of use of the chemical liquids (some of which are caustic).

Furthermore, the action of vacuum (the purpose of which is of enabling the liquid to penetrate, in order that it may come into contact with the material to be removed) and the feed of liquids and air into the vacuum system with variable-frequency pulses result in a particularly effective operation of total emptying of the pulp chamber and root canals.

Therefore, a peculiar and basic feature of the apparatus according to the present invention is that it should operate under vacuum and under atmospheric pressure, and by means of a pulsed flow of the liquid contained inside the sealed loop.

The results obtained from practical tests consist in the complete emptying of the pulp chamber and of the root canals independently from the shape and size of the latter, without having resort to any instruments for endocanal reaming.

The operation of sealing of the treated tooth, performed as disclosed hereinabove, prevents air bubbles from remaining inside the root canal, which would favour the arising of infections.

I claim:

1. Apparatus for carrying out devitalizations and root canal treatments in teeth, of the type in which liquid chemical treatment substances are fed into the pulp chamber and root canals of the tooth, characterized in that it comprises, in combination: sealing means for tightly sealing said pulp chamber, a tightly sealed vessel, means for putting said vessel under controlled vacuum, first selective connection means between said vessel and said pulp chamber, a plurality of atmospheric pressure containers suitable for containing respective liquids for the treatment of the pulp chamber and of the root canals, second selective connection means between said plurality of containers and said pulp chamber, and third selective connection means between said pulp chamber and atmosphere, so that the pulp chamber and the root canals can be firstly put under vacuum and then treated in succession with said treatment liquids at atmospheric pressure, which liquids are drawn into said vessel under controlled vacuum, flowing through said pulp chamber and the relevant root canals.

2. Apparatus according to claim 1 including means operative at short time intervals over a predetermined time period for changing the vacuum level inside said pulp chamber a plurality of times.

3. Apparatus according to claim 2, characterized in that said vacuum level changing means changes the vacuum level at a frequency of substantially 40 times per minute.

4. Apparatus according to claim 1 including means for connecting said pulp chamber selectively to said pressure containers at short time intervals over a predetermined time period.

5. Apparatus according to claim 4, characterized in that said pulp chamber connecting means selectively connects said pulp chamber to said pressure container at a frequency of substantially 20 times per minute.

6. Apparatus according to claim 1, characterized in that the values of vacuum inside the pulp chamber are within the range of from substantially 0.526 to 0.592 atm.

7. Apparatus according to claim 1, characterized in that is comprises, in combination: a vacuum pump (P), a pressure regulator (PR), a vacuum indicator (V), a limiting pressure regulator (RZ) comprising a device (Z) for warning that the limit safety vacuum has been reached, a tightly sealed vessel (10) acting both as a vacuum tank and as a collecting tank for the ill tissues removed, said plurality of atmospheric pressure containers including three containers (11, 12 and 13), each equipped with said second selective connection means including a respective electrovalve (14, 15 and 16) for selectively connecting each of said three containers with the pulp chamber (19) of a tooth (20), said second selective connection means further including an oscillator (17) with a control switch (37) which controls an electrovalve (18) for selectively connecting said vessel (10) with the pulp chamber (19) of said tooth (20), said pulp chamber sealing means includes a plug (21) suitable for tightly sealing the pulp chamber (19) of the tooth (20), into which a pair of ducts (22, 23) open which respectively connect the pulp chamber (19) with said vacuum vessel (10), said third selective connection means includes an electrovalve (24) controlled by an oscillator (25) which is in turn controlled by means of a switch (26), an air filter (27) in one of said pair of ducts (23), a central change-over switch (28) with respective multi-way switches (29, 30 and 31) for selecting the treatment liquid contained inside the containers (11, 12 and 13), pushbutton switches (32, 32 and 34) which enable the operator to respectively command, at time intervals, the opening of the electrovalves (14, 15 and 16), a main power switch (35), and a pushbutton switch (36) for controlling the electrovalves (14, 15 and 16).

8. Apparatus according to claim 7, characterized in that said ducts (22, 23) are provided with extensions (50, 51), with respective electrovalves (39, 40) for controlling the flow, and bypass ducts (48, 49) being installed between the ducts (22, 23) and the extensions (50, 51), with said electrovalves (39, 40) being piloted by means of a frequency generator (42), which is excited by a relay (41) controlled by means of a switch (38).

9. Apparatus according to claim 1, characterized in that said tightly sealed vessel is provided with connection means suitable for connecting said root canals with it.

10. Apparatus according to claim 9, characterized in that said connection means are constituted by at least one hollow needle connected with said vessel by means of a pipe, with the interposition of a piloted electrovalve.

11. Method for tightly sealing, by means of a paste-like substance, the pulp chamber and the root canals of a tooth previously submitted to devitalization and root canal treatment, characterized in that it comprises the steps of:
prearranging, inside the tooth, connection means suitable for connecting said root canals with a vacuum source;
filling the pulp chamber of the tooth with said paste-like substance, such as to tightly seal the underlying root canals;
connecting said connection means with the vacuum source;
applying vacuum to the interior of the root canals, such as to cause a portion of said paste-like substance, contained inside the pulp chamber, to be sucked into said root canals;
finally, removing said connection means from the tooth.

12. Method according to claim 11, characterized in that said connection means suitable for connecting the root canals with a vacuum source are constituted by hollow needles which are freely introduced into the root canals before the paste-like substance for treatment and filling is fed into the pulp chamber.

13. Method according to claim 11, characterized in that said vacuum source is connected with the hollow needles through of a pipe which ends with a fitting for its tight connection with the same needles, and with the interposition of an electrovalve which controls the application of vacuum.

14. Method according to claim 11, characterized in that the vacuum source is constituted by a vessel which is evacuated by means of a vacuum pump, and is connected with the hollow needles by means of a pipe ending with a fitting for tightly connecting said pipe with the same needles, and with the interposition of an electrovalve which controls the application of vacuum.

* * * * *